United States Patent [19]

Fischer et al.

[11] Patent Number: 4,478,579
[45] Date of Patent: Oct. 23, 1984

[54] SNUGLY FITTING DENTURE AND PROCESS OF ITS MANUFACTURE

[75] Inventors: Wolfgang Fischer, Radeberg; Gerhard Gehre, Leipzig; Rainer Korf, Radeberg; Renate Lorenz, Radeberg; Heinz Täschner, Radeberg, all of German Democratic Rep.

[73] Assignee: VEB Kombinat Medizin- und Labortechnik Leipzig, Leipzig, German Democratic Rep.

[21] Appl. No.: 362,738

[22] Filed: Mar. 29, 1982

[30] Foreign Application Priority Data

Jun. 4, 1981 [DD] German Democratic Rep. ... 230576

[51] Int. Cl.³ ........................ A61C 5/08; A61C 5/10
[52] U.S. Cl. ..................................... 433/222; 433/223
[58] Field of Search ............... 433/202, 203, 206, 208, 433/218, 222, 223; 264/16, 18, 19

[56] References Cited

U.S. PATENT DOCUMENTS

| | | | |
|---|---|---|---|
| 2,930,125 | 3/1960 | Pos | 433/223 |
| 3,423,829 | 1/1969 | Halpern et al. | 433/212 X |
| 4,104,798 | 8/1978 | Takahashi et al. | 433/222 |
| 4,364,731 | 12/1982 | Norling et al. | 433/223 X |
| 4,398,007 | 8/1983 | Kubota et al. | 433/202 X |

FOREIGN PATENT DOCUMENTS 2211382 9/1972 Fed. Rep. of Germany ...... 433/202

*Primary Examiner*—Robert P. Swiatek
*Attorney, Agent, or Firm*—Jordan and Hamburg

[57] ABSTRACT

The invention concerns a snugly fitting denture such as bridges and the like, consisting of a metallic foundation and of a ceramic facing shell as well as a process to its manufacture. It is the object of this invention to develop a compact system for a snugly fitting denture with high firmness and mechanical loading capacity as well as with prolonged durability under the conditions prevailing in the oral cavity. This is achieved by the fact that the metallic foundation consists of a base metal alloy with a silane-content of ≦0.5% and that the ceramic facing shell is provided with a silicon-coupled adhesive plastic part. The metal base is silanized in an ultrasound bath, highly fluid prosthesis plastic is applied to its labial aspect and the facing shell is pressed-on. Thus a solid chemical bonding develops between foundation and facing shell. This compact system is without slits and does not offer any possibilities of aggression to harmful influences existing in the milieu of the oral cavity.

16 Claims, 2 Drawing Figures

SNUGLY FITTING DENTURE AND PROCESS OF ITS MANUFACTURE

BACKGROUND OF THE INVENTION AND PRIOR ART STATEMENT

The invention concerns a snugly fitting denture such as bridges and the like, consisting of a metallic foundation and a ceramic facing shell, which is silanized and fixed to the foundation by means of cold-polymeride, as well as a process for its manufacture.

Denture materials which have stood the test of time are plastic (mostly derivatives of polymethyl methacrylate) alloys (noble metals and other alloys of base metals being resistant to the conditions prevailing in the oral cavity) and ceramic materials. Most of these aids to therapy are built up from several materials and their clinical usefulnss is determined to a decisive extent by their compactness.

While the homologous joining of materials (metal to metal, plastic to plastic, ceramic to ceramic) is largely without problems during processing in the dental laboratory, heterogeneous combinations of materials may lead to difficulties if its adherence should surpass the firmness of pure mechanical retention. In this context the joining of metal to ceramic (e.g. DE-OS 2 106 013) and the joining of plastic to ceramic according to DD-WP 148 857 could be considered as being solved during the last decades. According to which a mineral tooth with silane coupled adhesive plastic part is proposed in which the basic materials of the individual layers of the mineral tooth have grain sizes in a fractionation from less than 60 $\mu$m to 100 $\mu$m. The adhesive plastic part applied to the silane layer consisting of a multicomponent mixture made of polymethacrylic acid methylester, dioxane, methacrylic acid methylester, a sensitizer and a vapour pressure reducer are arranged in the dorsal and basal areas respectively of the mineral tooth. The mineral tooth is immersed several times into the silane solution and dried subsequently and thereafter the multicomponent mixture is applied to the dorsal and basal areas respectively of the presilanized mineral tooth without any pressure using a source of heat radiation with temperatures between 20° and 50° C. and during a period of time between 3 and 6 minutes and is polymerized without pressure. Heretofore the results of attempts to join plastic with metals in a slitless manner are not satisfactory. This combination of materials is of particular importance with toothcoloured facing of metallic materials within the frame of the technique using crowns and bridges (firmly fitting dentures). Here defective joining will lead to premature separation of the facing, formation of marginal slits with exogenous discolouring of the plastic (due to oxidation of the metal scaffolding and seeping-in of colouring substances), restricted biocompatibility due to mechanical irritation of tissue at the slit between facing and scaffolding, formation of plaques and increased bacterial settlement.

The prerequisites of the firmness of the joining depend on the load imposed by clinical use. To these belong predominantly physical-mechanical loads, influences due to saliva, foodstuffs, drugs, microbes and changing temperatures. Factors influencing adherence on the part of materials are polymerization of plastic, shrinking due to polymerization, differences in temperature and density, time, viscosity of processing, elastic properties of plastic and pretreatment of adhesive areas.

Until now the problem of adherence of metal to plastic under the conditions of the oral cavity is still unsolved. Using the known compounds, mechanical anchoring and at best adhesion may be anticipated. In order to prevent separation of plastics, which were polymerized onto metals, space-occupying and indication restricting retentions with sites extending under themselves are necessary. Thus separation may be prevented in general, but not the formation of slits. According to publication DE-OS 2 162 608 an agent is known, which serves for covering of metal scaffoldings and of butt metal for plastic facings for dental prosthetics consisting in essentially of a mixed polymeride from about 20 to 60 parts w/w acrylonitrile and 40 to 60 parts w/w of methylmethacrylate. In addition the mixed polymeride contains up to 5 parts w/w of methacrylic acid as well as 0.01 to 1 part w/w of a silicon hydrogen compound for improving adherence. The process for opaquization of the metal foundation for crowns and bridge-prosthesis is characterized by the fact, that the mixed polymeride is dissolved in a solvent consisting of nitroparaffins and/or halogenated hydrocarbons, an opaquization pigment is dispersed in this solvent as well as an adhesion improving agent $\gamma$-methacryloxipropyl trimethoxysilane and the resulting agent is applied to the surface of a dental metal alloy foundation, of a noble-metal or of a noble-metal alloy. When the solvent has escaped a dental resin for crowns or bridges is applied in a methyl methacrylate monomer-carrier at the opaquized surface for the manufacture of dental products.

Due to the good results, which were obtained with the use of silanes as mediator of adherence, it was proposed for the manufacture of crowns and bridges the basic scaffoldings of which consist of metallic materials to use prefabricated mineral facets, which are silanized and are fixed by means of a cold polymeride to the metallic bridge scaffolding. Adherence of hot polymerized plastics is particularly poor because of additional tensions due to shrinking, because of cooling down, although this plastic material is distinguished by improved durability under the conditions prevailing in the oral cavity. Pressure-heat-polymerization which was recommended recently also diminishes the size of the slits only, but does not prevent them.

Better is the firmness of joining of cold plastics, which occasionally develop a certain adhesive power. The more thin the applied layers of plastic the lesser are the tensions depending on shrinking due to polymerization. However cold plastics also show a considerable drop in adhesive properties after storage in water under the conditions prevailing within the oral cavity.

Adhesive lacquers and coating lacquers which were recommended in order to improve adhesive strength and reduction in slit formation, have not proven to be satisfactory. Silanes applied in a thin layer onto the metal as so-called primers have also been recommended, but until now have not found general introduction.

The aim of the invention is to avoid the disadvantages of the solutions known until now and to provide for a snugly fitting denture, which while fulfilling high aesthetic demands may be manufactured in dental laboratories with a small economic expenditure.

SUMMARY OF THE INVENTION

It is the scope of this invention to develop a compact system for snugly fitting dentures with high adhesive power and mechanical loading capacity as well as with good prolonged durability under the conditions prevailing in the oral cavity. Furthermore it is the task of the invention to describe a process for the manufacture of a snugly fitting dental prosthesis.

According to the invention the problem is solved by the fact that the metallic foundation consists of an alloy from a base metal having a silicon content of $\leq 0.5\%$, that the ceramic facing shell is provided with a silane coupled adhesive plastic part, that the metallic foundation is silanized and that on the silane layer of the metallic foundation at the labial aspect a tooth coloured layer of prosthesis plastic is arranged.

In the preferred version the prosthesis plastic has the consistency of a highly fluid substance. The incisal edge of the facing shell surrounds the metallic foundation. In a further version the incisal edge of the facing shell is grinded and shows a marginal border with the incisal edge of the metallic foundation.

The process of manufacture according to the invention is carried out by immersion of the metallic foundation for one or several times into a silane solution and is dried-up thereafter, at the labial aspect the prosthesis plastic is applied to the silane layer in an uniformly thin manner and subsequently with the silane coupled adhesive plastic part being manufactured by a known process provided with the facing shell is pressed-on and the prosthesis plastic is polymerized.

It is advantageous to roughen the surface of the metallic foundation by sand blasting and to perform silanization in an ultrasonic bath.

BRIEF DESCRIPTION OF THE DRAWINGS

In the following the invention will be described into more detail. The pertaining drawings illustrate FIG. 1 a snugly fitting denture with a cupola-like incisal edge FIG. 2 a snugly fitting denture with a ground incisal edge.

DETAILED DESCRIPTION OF PREFERRED EMBODIMENTS

Figure 2:
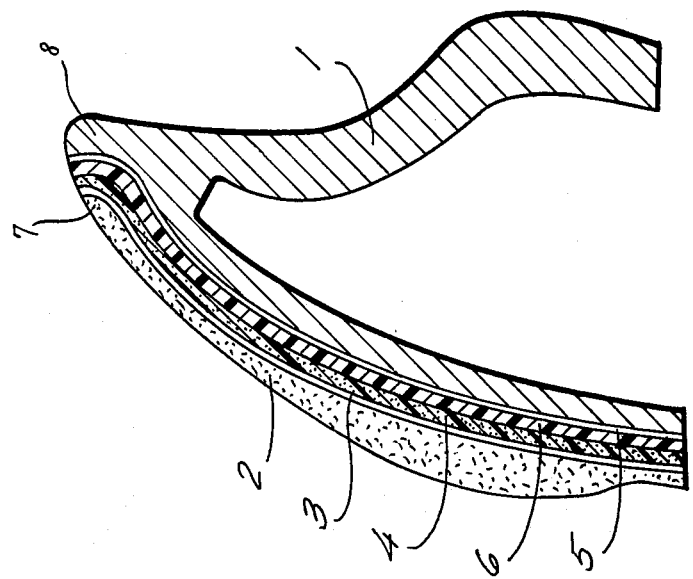
Figure 1:
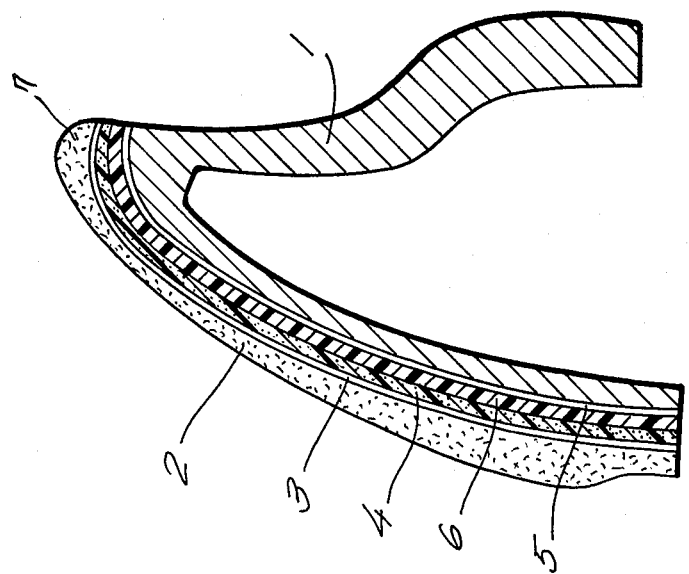

The snugly fitting denture as illustrated in FIGS. 1 and 2 consists of the metallic foundation 1 and of a ceramic facing shell 2. For the metallic foundation 1 dental base metal alloys of the basic types nickel-chromium, iron-chromium and cobalt-chromium-molybdenum with a silicon-content of $\leq 0.5\%$ are used. The ceramic facing-shell 2 is provided with a silane layer 3 and an adhesive plastic part 4. On the metallic foundatin 1, a tooth-coloured layer of prosthesis plastic 6 is applied. In order to minimize the volume contraction during the process of polymerization of the plastic material, the layer of prosthesis plastics 6 has to be of a small thickness and for the prosthesis plastic an ascension-ratio has to be chosen, which is highly fluid in its consistency.

According to FIG. 1 the incisal edge 7 of the ceramic facing shell 2 surrounds the metallic foundation 1 in a cupola-like manner.

In FIG. 2 the incisal edge 7 of the ceramic facing shell is ground in a manner providing a junction in the incisal edge 8 of the metallic foundation 1.

The process of manufacture according to the invention proceeds in the following manner:

After the casting of the metal foundation 1 the casting scale is removed by means of sand blasting, causing a greater surface roughness and thus increasing the effective surface of adherence in an aimed at manner.

After thorough degreasing by means of 1,1,2-trifluorotrichloroethane or using other solvents and subsequent drying the metallic foundation 1 is silanized. It is most favourable to silanize twice using ultrasound in a silane solution. The silane solution preferentially is composed of $\gamma$-methacryloxipropyltrimethoxisilane in a medium which is acidified by acetic acid.

Onto the silane layer 5 of the foundation 1, the tooth coloured prosthesis plastic (cold or hot plastic) which is known in dental prosthetics, is subsequently applied. Facing of the metallic foundation is effected by pressing of the ceramic facing shell 2 with the silane-coupled adhesive plastic part onto the prepared layer of prosthesis plastic 6.

The polymerizing of the ceramic facing shell 2 with silane-coupled adhesive plastic part 4 is effected depending on the use of either cold- or hot plastic according to the processing procedure being known for this particular prosthesis plastic. This plastic material enters into a firm chemical compound with the silanized silane-containing metallic foundation. On the other hand, by means of the process of polymerisation, a firm connection is made to the adhesive plastic part 4 of the ceramic facing shell 2. The facing shell 2 with silane coupled adhesive plastic part 4 is preferentially manufactured on an industrial scale according to the known process as described in DD-WP 148 857 but may be manufactured individually in a dental laboratory also.

The compact system as manufactured according to the above mentioned process is characterized by a firm chemical bonding in between the individual layers. It is thus without any slits and does not offer any possibility of aggression to harmful influences existing in the milieu of the oral cavity.

An increased long term durability of the compact system facing shell-metallic foundation is achieved by the additional mechanical anchoring of the plastic layer to the metal, which arises due to the penetration of the plastic material into smallest hollow spaces of the surface cleaned by sand blasting.

Due to the cupola like shaping and grinding respectively of the incisal edge of the ceramic facing shell and the corresponding adjustment of the metallic foundation an almost complete marginal closure between facing shell and foundation is provided. This marginal closure serves the purpose of preventing harmful influences of the milieu of the oral cavity on the double sided coupled adhesive plastic part including the mechanism of coupling.

We claim:

1. A process of producing a snugly-fitting denture, comprising
   (A) immersing a metallic foundation in a silane solution at least once,
   (B) drying said metallic foundation, whereby a silane layer is formed on said metallic foundation,
   (C) applying in a uniformly thin manner a prosthetic plastic to the labial aspect of said silane layer formed on said metallic foundation,
   (D) providing a ceramic facing shell with a silane-coupled, adhesive plastic portion,
   (E) pressing said facing shell with said silane-coupled, adhesive plastic portion onto said prosthetic plastic; and
   (F) polymerizing said prosthetic plastic to said silane-coupled adhesive plastic portion, so that a firm bonding is made, and so that said metallic foundation is fixed to said ceramic facing shell.

2. The process of claim 1 in which the surface of the metallic foundation is initially roughened by sand blasting prior to step (A).

3. The process of claim 1 in which the metallic foundation comprises a dental base metal alloy selected from the group consisting of nickel-chromium, iron-chromium and cobalt-chromium-molybdenum, said base metal alloy having a silicon content of less than 0.5%.

4. The process of claim 1 in which the silane solution comprises γ-methacryloxipropyl trimethoxysilane in a medium which is acidified by acetic acid, so that the silane layer formed on the metallic foundation is essentially composed of γ-methacryloxipropyl trimethoxisilane.

5. The process of claim 1 in which the metallic foundation is immersed twice in the silane solution.

6. The process of claim 1 in which step (A) is performed in an ultrasonic bath.

7. The process of claim 1 in which the prosthetic plastic is a tooth colored prosthesis plastic.

8. The process of claim 1 in which the prosthesis plastic has an ascension-ratio such that the prosthesis plastic has the consistency of a highly fluid substance.

9. The process of claim 1 in which the polymerization of step (F) is cold-polymerization.

10. The process of claim 1 in which the ceramic facing shell of the snugly-fitting denture has an incisal edge, said incisal edge surrounding the metallic foundation in a cupola-like manner.

11. The process of claim 1 in which both the metallic foundation and the ceramic facing shell of the snugly fitting denture have an incisal edge, said incisal edge of the ceramic facing shell being ground in a manner to provide a junction in, and to show a marginal border with, said incisal edge of the metallic foundation.

12. A snugly fitting denture, comprising a metallic foundation, said metallic foundation being essentially composed of a dental base metal alloy having a silicon content of less than 0.5%, a first silane layer disposed on said metallic foundation, a first plastic layer disposed on the labial aspect of said first silane layer, whereby said first plastic layer is attached to said metallic foundation by said first silane layer, said first plastic layer comprising a tooth colored prosthesis plastic having an ascension-ratio such that the prosthesis plastic has the consistency of a highly fluid substance, a second plastic layer disposed on said first plastic layer, said second plastic layer being an adhesive plastic portion which is firmly bound to said first plastic layer by cold polymerization of said first plastic layer, a second silane layer disposed on the side of said second plastic layer opposite to said first plastic layer, and a ceramic facing shell, said ceramic facing shell being coupled to said second plastic layer by said second silane layer.

13. The snugly fitting denture of claim 12 in which the base metal alloy is selected from the group consisting of nickel-chromium, iron-chromium and cobalt-chromium-molybdenum.

14. The snugly fitting denture of claim 12 in which the first and second silane layers are essentially composed of γ-methacryloxipropyl trimethoxisilane.

15. The snugly fitting denture of claim 12 in which the ceramic facing shell has an incisal edge, said incisal edge surrounding the metallic foundation in a cupola-like manner.

16. The snugly fitting denture of claim 12 in which both the metallic foundation and the ceramic facing shell have an incisal edge, said incisal edge of the ceramic facing shell being ground in a manner to provide a junction in, and to show a marginal border with, said incisal edge of the metallic foundation.

* * * * *